United States Patent
Tomita et al.

(10) Patent No.: US 6,319,895 B1
(45) Date of Patent: Nov. 20, 2001

(54) LACTOFERRIN TABLETS

(75) Inventors: Mamoru Tomita; Ryo Kato; Yuzo Asano; Kenji Nishi; Yuriko Iiyama; Tsutomu Kudo, all of Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 09/341,316

(22) PCT Filed: Jan. 8, 1998

(86) PCT No.: PCT/JP98/00024
§ 371 Date: Sep. 2, 1999
§ 102(e) Date: Sep. 2, 1999

(87) PCT Pub. No.: WO98/30235
PCT Pub. Date: Jul. 16, 1999

(30) Foreign Application Priority Data

Jan. 9, 1997 (JP) .................................................. 9-013429

(51) Int. Cl.[7] ............................ A61K 38/40; A61K 9/20; A61K 31/70; A61K 35/20; A61K 35/74; C12N 1/00

(52) U.S. Cl. ............................ 514/8; 424/93.1; 424/93.3; 424/93.4; 424/93.44; 424/93.45; 424/464; 424/465; 424/535; 514/23; 514/25; 514/53; 435/822; 435/853; 435/885

(58) Field of Search ................................. 424/93.4, 93.44, 424/93.45, 465, 464, 93.1, 93.3, 535; 514/2, 8, 23, 29, 93; 435/822, 893, 885

(56) References Cited

U.S. PATENT DOCUMENTS

| 4,767,623 | * | 8/1988 | Conway et al. | 424/93 |
| 5,322,836 | * | 6/1994 | Tomita et al. | 514/6 |
| 5,501,861 | * | 3/1996 | Makino | 424/464 |
| 5,624,906 | * | 4/1997 | Vermeer | 514/23 |

FOREIGN PATENT DOCUMENTS

| 1-221319 | 9/1989 | (JP) . |
| 6-040922 | 2/1994 | (JP) . |
| 8-208517 | 8/1996 | (JP) . |

* cited by examiner

Primary Examiner—Jose' G. Dees
Assistant Examiner—Frank Choi
(74) Attorney, Agent, or Firm—Wenderoth, Lind & Ponack, L.L.P.

(57) ABSTRACT

Lactoferrin tablets comprising as the active ingredients lactoferrin and lactulose and having a horizontal hardness of at least 4 kg and a vertical hardness of at least 3 kg; and lactoferrin tablets comprising as the active ingredients a microbial cell powder of at least one microorganism selected from among lactic acid bacteria, lactoferrin and lactulose and having a horizontal hardness of at least 4 kg and a vertical hardness of at least 3 kg. These tablets can be produced by using the conventional tableting apparatuses and yet have high hardness. Thus, they do not adhere to the inner wall of the oral cavity and have a favorable taste. Since no excessive tableting pressure is needed in the production process, moreover, these tablets can contain much viable cells of lactic acid bacteria, though they are in the form of rigid tablet.

8 Claims, No Drawings

LACTOFERRIN TABLETS

This application is a 371 of PCT JP98/00024, filed Jan. 18, 1998.

BACKGROUND OF THE INVENTION

1. Field of the Invention

This invention relates to a lactoferrin table. More particularly, this invention relates to a lactoferrin tablet having such pharmacological actions as protection of infection and immunopotentiation and, in addition, having very high hardness.

2. Description of the Related Art

Lactulose is a kind of disaccharide (4-O-β-D-galactopyranosyl-α-fructose) consisting of galactose and fructose and is produced by subjecting lactose to a Lobry de Bruyn transformation. Lactulose has been known as a growth factor for bifidobacteria (Shindan to Shinyalu, volume 80, number 5, page 75, 1973) and used in a modified dry milk, dry milk for the weaning period, etc. In addition, lactulose has been known to have an action of reducing the symptoms of hepatic encephalopathy and hepatic coma, and has been used for the therapy already (Seishirl Igaku, volume 15, number 10, page 1101, 1973).

However, it has not been known yet that lactulose is effective as an excipient for increasing the hardness of tablets.

On the other hand, lactoferrin is a non-toxic and natural iron-binding protein contained in tear, saliva, peripheral blood, milk, etc and has been known to have an antimicrobial action to toxic microorganisms such as Escherichia coli, Candida, Closttidium, etc. (Journal of Pediatrics, volume 94, page 1, 1979). It has been also reported that lactoferrin is effective for staying useful microorganisms such as bifidobacteria and lactobacillus to intestine of human being and animals (Japanese Patent No. 2,532,911).

Up to now, lactoferrin has been compounded in modified dry milk for babies and small children, etc. and, with regard to one of the means for adults to take the necessary dose easily, and conveniantly, an art concerning lactoferrin-containing powder (Japanese Patent No. 2,532,911) and granules (JP 8-253423 A) has been known. Further, as one of the methods for making the oral administration of powdery lactoferrin easy, it has been known to make it into tablets (Drug Topics, Sep. 9, 1996), and tablets containing Lactoferrin have been put into the market since October 1996.

Incidentally, a tablet is usually easily taken as one dosing unit, can be easily administered and is relatively easily produced and, because of such reasons, tablets are utilized in many pharmaceuticals, health foods, etc. After being produced. tablets are packed and transported and, since the tablets receive considerable force from outside such as shaking and impact during such steps, they are to be made for having an appropriate mechanical strength so that the tablets are not disintegrated and keep their commercial value.

When a tablet containing lactoferrin is taken by chewing, broken pieces of the tablet adhere to the inner wall of the oral cavity such as teeth upon chewing resulting in a decrease in a favorable taste whereby the taste significantly decreases unless the tablet has hardness of some extent.

Hardness of tablet is measured by disintegration using a conventional method by applying a static pressure to a horizontal direction and a load to a vertical direction and hardness of each direction is expressed in a unit of kg. The vertical direction is a direction in which a pestle compresses the material upon tableting, while the horizontal direction is a direction in a right angle to the horizontal direction.

In the commercially available lactoferrin-containing tablets, their hardness in the horizontal direction is about 3.1 kg in average while that in the vertical direction is about 1.6 kg in average. Thus, the hardness is extremely low and this is a big problem in terms of the rigidity of the tablet.

The inventors of this application have conducted many attempts for the manufacture of tablets according to conventional methods by adding known excipients such as a starch (e.g. corn starch) and a saccharide (e.g., lactose and sucrose) to lactoferrin but obtained tablets having only low hardness.

The inventors further tried tableting by a conventional method using granules which were prepared by granulating a mixture of all of or a part of materials for the tablets. In that case, hardness increased and improvement in the tablet hardness was noted as compared with the already-mentioned case where the powdery materials are directly tableted although the result was still unsatisfactory as stable tablets which are durable for transportation as a commercial product.

As one of the means for increasing the hardness of tablets, an increase in the tableting pressure was known (Iyakuhin Kaihatsu Kiso Koza—Seizai Kogaku [Elementary Textbook on Development of Pharmaceuticals—Tablet Manufacturing Technology], page 156, published by Chijin Shokan, 1971). However, in making a lactoferrin-containing composition into tablets, an excessive tableting pressure is not favorable because it causes a capping (detachment of the upper surface of tablets), lamination (detachment in layers), etc. upon tableting and there is a problem of causing a decrease in the remaining number of viable cells in making a composition containing viable microbial powder of lactobacillus into tablets.

SUMMARY OF THE INVENTION

An object of this application is to provide a tablet containing lactoferrin as an active ingredient where the tablet has high hardness, does are not disintegrated during transportation and does not adhere to the inner wall of oral cavity upon taking.

In order to achieve the above-mentioned object, this application provides an invention which is a lactoferrin tablet comprising lactoferrin and lactulose as the active ingredients, and having a horizontal hardness of at least 4 kg and a vertical hardness of at least 3 kg.

This application also provides a second aspect of the above invention, which is a lactoferrin tablet comprising at least one kind of microbial powder selected from the group consisting of microorganisms belonging to Bifidobactenum, microorganisms belonging to Lactobacillus, microorganisms belonging to Streptococcus, microorganisms belonging to Pediococcus and microorganisms belonging to Leuconostoc together with lactoferrin and lactulose as the active ingredients, and having a horizontal hardness of at least 4 kg and a vertical hardness of at least 3 kg.

In the lactoferrin tablet of the above-mentioned first and second aspects of the present is, it is a preferred embodiment that the hardness of the tablet in the horizontal direction is 6–14 kg and that in the vertical direction is 5–14 kg.

In addition, it is another preferred embodiment that at least 0.05 part of lacts (hereinafter, the term "part(s)" stands for that/those by weight unless otherwise mentioned) is contained to 1 part of lactoferrin.

Incidentally, the hardness in horizontal and vertical directions of the lactoferrin tablet in the above-mentioned first and second aspects of the present invention is the value which is measured by the same method as in the common measuring method for hardness of tablets as mentioned already.

DESCRIPTION OF THE PREFERRED EMBODIMENTS

With regard to lactferrin and lactulose used in the first and the second aspects of this application, those which are commercially available or manufactured by known methods may be used. For example, lactoferrin can be produced as follows by a method disclosed in JP 6-13560 B.

Skim milk or milk which is prepared from cow's milk is contacted at the temperature of 0–60° C. with a weakly acidic cationic exchanger having a carboxyl group as an ion-exchanging group and having a hemoglobin-absorbing ability of not less than 3.5 g/100 ml, and the weakly acidic cationic exchanger is washed with water. Thereafter, a salt solution is passed through the weakly acidic cationic exchanger to desorb the lactoferrin from the weakly acidic cationic exchanger, and the eluate is desalted and freeze-dried. According to this method, it is possible to produce lactoferrin having a high purity of not less than 98% (by weight).

With regard to lactulose, crystals of lactulose trihydrate disclosed In JP 5-43590 A and JP 6-107675 A and anhydrous lactulose crystals can be advantageously used. The anhydrous lactulose crystals can be produced from an alcoholic solution of lactulose according to known methods (*Journal of the Affect Chemical Society*, volume 52, page 2101, 1930, or U.S. Pat. No. 4,536,221) From an aqueous solution, it can be produced as follows according to the methods disclosed, for example, in JP 3-169888 A and JP 6-228179A.

Sodium hydroxide is added to a 10% aqueous solution of commercially available lactose. followed by mixing, and thereafter the mixed solution was heated at 70° C. for 30 minutes and cooled. The cooled solution was purified by an ion-exchange resin, concentrated, cooled and crystallized and the unreacted lactose is removed to give an aqueous solution of lactulose in which the solid content is about 68% (where the solid contains about 79% of lactulose). This aqueous solution is passed through a column filled with a strongly acidic ion-exchange resin and a fraction containing lactulose is collected and concentrated to give an aqueous solution of pure lactulose containing about 68% of solid (where the solid contains about 86% of lactulose). This is the method disclosed in JP 3-169888 A.

The aqueous solution (syrup) of lactulose obtained by the above method is concentrated to an extent of a solid content of about 72%. The concentrated solution is cooled at 15° C. Crystals of lactulose trihydrate are added thereto as seed crystals. The mixture is gradually cooled to 5° C. in seven days with stirring to grow the crystals and, after ten days, the crystals are separated using a centrifugal separator of a filter cloth type from a liquid where the solid content of the supernatant liquid is decreased to about 61%, washed with cold water of 5° C. and dried to give crystals of lactulose of not lower than 95% purity. This is a method disclosed in JP 6-228179 A.

Besides the above, anhydrous lactulose crystals can be produced from crystals of lactulose trihydrate by a method disclosed in JP 5-111400 A as well. It is desirable that the lactulose used in this invention is as pure as possible and it is particularly desirable that the purity is not lower than 95%.

Lactoferrin produced as above is contained in an amount of 5–900 mg, preferably 50–800 mg per one gram of the tablet. In this invention, at least 0.05 part and 100 parts at most, preferably 0.10–10 parts of lactulose is contained to one part of lactoferrin.

In the lactoferrin tablet of the first and the second aspects of the present invention, appropriate amounts of other ingredients such as lubricant (e.g., sucrose fatty acid ester and glycerol fatty acid ester) and ingredients for improving the taste and the feel on eating (e.g., saccharide, sweetener, perfume, thickener, emulsifier, etc.) are added to prepare materials for the tablet.

The above materials for the tablet may be disintegrated using a known disintegrating machine [for example, a rotary pin mill (manufactured by Hosokawa Micron)] or, prior to a tableting, it may be previously granulated using a known granulator such as an extruding granulator [for example, an extrude-o-mix (manufactured by Hosokawa Micron)] or a fluidized bed granulator [for example, a Grat fluidized granulating drier (manufactured by Okawara Seisakusho)], followed by tableting. However, it is preferred that lubricant, perfume, viable microbial powder of lactic acid bacteria which will be mentioned later, etc. are not granulated.

As mentioned above, the tablet material prepared is tableted by known method and apparatus. A machine used for the tableting is a tableting machine in a powder-compressing type and any of known rotary tableting machine, eccentric tableting machine, etc. may be used although it is preferred to use a rotary tablating machine for a production in an industrial scale. To be more specific, for example, the tablet material prepared as above is supplied to a rotary tableting machine [such as a small high-speed tableting machine of an HT-PA type (manufactured by Hata Tekkosho), etc.], compressed between the upper and the lower pestles having a desired tablet shape and molded whereupon tablets are prepared. The compressing pressure upon tableting (what is called the tableting pressure) varies depending upon the composition of the tableting material, tablet shape, tableting speed, type of tableting machine, etc. but, usually, it is within the range of from 1 ton to 5 tons. It is also possible that, immediately before the tableting, the tableting material may be preliminarily compressed with a pressure of about 1 ton.

With regard to the shape of tablets, although the strength may decrease a little when the shape is extremely unusual, it is possible to make into a shape which is commonly used for tablets such as circle, triangle, polyhedron, football-shape, buccal-shape, flower-shape, heart-shape, etc.

The microbial powder of lactic acid bacteria used for the lactoferrin tablet according to the second aspects of the present invention may be any of viable microbial powder or dead microbial powder but, in view of having a controlling action to intestinal function in vivo, viable microbial powder is preferred. With regard to microbial powder of lactic acid bacteria, commercially available one or that which is prepared by known methods (for example, a method disclosed in JP 1-221319 A) may be used. Preparation of the microbial powder may be carried out, for example, as follows. Thus, a preculture of the desired microorganism is carried out in large quantities by a conventional method and a freeze-drying is conducted after adding a dispersing medium having a protecting action depending upon the microorganism separated from the culture liquid such as saccharide, amino acid, starch, gelatin, skimmed milk, etc. if necessary whereupon dry microbial cells are prepared. More detailed method of preparing the microbial powder of lactic acid bacteria is given in Referential Examples 1–4 which will be mentioned later.

In the lactoferrin tablet of the second aspects of the present invention, it is preferred that 0.01–1 part of microbial powder of lactic acid bacteria is used per 1 part of a mixture of lactoferrin and lactulose in terms of maintaining the viable microbial cell numbers necessary in the tablet and of hardness of the tablet. In addition, in the lactoferrin tablet of the second aspects of the present invention, an excessive tableting pressure is not necessary and, therefore, there is a big advantage that a large amount of lactic acid bacteria cells can be contained in a state of viable cells as mentioned already.

The lactoferrin tablet of the first and the second aspects of the present invention which are produced as such have high hardness and abrasion resistance and, therefore, they are able to be charged and packed regardless of packing forms such as bottles, cans, bags, blister package, etc. and also able to prevent damage, disintegration, etc. during transportation.

In this invention, since lactulose is added to the lactoferrin tablet as such, the tablet have high hardness in each of horizontal and vertical directions, are well resistant to impact by transportation and handling upon tableting and packing, and are able to improve the productivity and the product quality and, in addition, they are good in terms of actual use such as no adherence to oral cavity upon taking and have characteristics which have not been available in the conventional products, in spite of the fact that lactoferrin is contained therein.

Now the invention will be illustrated by way of the following Tests. However, these Tests are merely illustrative and should not be construed to limit the spirit and scope of the claims.

Test 1.

This test was carried out for determining the effect of lactulose on hardness of the lactoferrin tablet.

1) Preparation of the Samples

Glycerol fatty acid ester (manufactured by Riken Vitamin) (3 parts) was added as a lubricant to 97 parts of a mixture where lactulose powder (manufactured by Morinaga Milk Industry) was compounded with lactoferrin powder (manufactured by Morinaga Milk Industry) in a ratio of 0.5:1, followed by homogeneously mixing to prepare a tablet material (Sample 1).

Separately, glycerol fatty acid ester (manufactured by Morinaga Milk Industry) (3 parts) was added as a lubricant to 97 parts of a mixture where erythritol powder (manufactured by Nikken Kagaku) or maltitol powder (manufactured by Towa Kasei Kogyo) was compounded with lactoferrin powder (manufactured by Morinaga Milk Industry) in a ratio of 0.5:1, followed by homogeneously mixing to prepare a tablet material (Samples 2 and 3).

Each of the Samples was made into tablets with a tableting pressure of 2 tons using a tableting machine of a rotating table type (manufactured by Hata Tekkosho) equipped with round pestles for tablets having a diameter of 10 mm whereupon 500 round-shaped tablets each having a diameter of 10 mm and a weight of 0.5 g were prepared for each of the Samples.

2) Procedures

From each of the Samples, 30 tablets were randomly sampled, the hardness of each tablet in horizontal and vertical directions was measured by a digital hardness tester (manufactured by Kiya Seisakusho) and average of each Sample was calculated whereby a comparative test regarding the hardness was carried out.

3) Results

The results of the test were that the tablets using erythritol (Sample 2) was very fragile and their average hardness in the horizontal direction and that in the vertical direction were 0.5 kg and 0.3 kg, respectively. The average hardness of the tablets (Sample 3) where maltitol which is commonly used as a excipient for tablets was used was higher than that of the above Sample 2 and that in the horizontal direction and in the vertical direction were 3.0 kg and 1.2 kg, respectively.

In contrast to that, the average hardness of the tablets where lactulose was added (Sample 1) was 10 kg in the horizontal direction and 8 kg in the vertical direction whereby a significant increase in the hardness of tablets by the use of lactulose was noted.

The same tests were carried out for the tablets prepared by changing the types of lactoferrin, lactulose and tableting machine whereupon nearly the same results were obtained.

Test 2.

This test was carried out for checking the ratio of lactulose to lactoferrin which is suitable for preparing the tablet.

1) Preparation of the Samples

The same method as in Test 1 was conducted except that 97 parts of a mixture where lactulose powder (manufactured by Morinaga Milk Industry) was compounded with lactoferrin powder (manufactured by Morinaga Milk Industry) in a ratio of 0–0.95:1 to prepare round-shape tablets each weighing 0.5 g. In addition, the same method as in Test 1 was conducted except that lactoferrin powder was not used but only 97 parts of lactulose powder (manufactured by Morinaga Milk Industry) were used to prepare round-shaped tablets each weighing 0.5 g.

2) Procedures

An average hardness was measured by the same method as in Test 1.

3) Results

The results are shown in Table 1. It is apparent from Table 1 that, when 0.05 part or more lactulose was added to 1 part of lactoferrin, a tablet having a hardness which is durable against the impact during transportation, etc. (4 kg in average in the horizontal direction and 3 kg in average in the vertical direction) were obtained and that, when 0.10 part or more was added, the rigid tablets having a hardness of not less than 6 kg in the horizontal direction and not less than 5 kg in the vertical direction were obtained. When 100 parts of lactulose were added to 1 part of lactoferrin, the hardness of the tablets was 15 kg in average in both horizontal and vertical directions and the tablets similar to those where no lactoferrin was added (16 kg in average in both horizontal and vertical directions) were obtained.

In each of the resulting tablets where the added amount of lactulose was 0.03 part to 1 part of lactoferrin, all of the samples showed an adhesion to teeth upon chewing. On the contrary, when the added amount was 0.05 part, the adhesion was rarely noted and, when the amount was 0.10 part or more, no adhesion was noted at obtained.

Accordingly, it has been found that, as a result of addition of at least 0.05 part, preferably 0.10–10 part(s) of lactulose to 1 part of lactoferrin, the rigid tablets having a hardness of 6–14 kg in the horizontal direction and 5–14 kg in the vertical direction were obtained.

The same tests were carried out for the tablets prepared by changing the types of lactoferrin, lactulose and tableting machine whereupon nearly the same results were obtained.

TABLE 1

| Compounding Ratio (parts by weight) | | Hardness of Tablets (kg) | |
|---|---|---|---|
| Lactoferrin | Lactulose | Horizontal Direction | Vertical Direction |
| 1 | 0 | 0.2 | 0.1 |
| 1 | 0.03 | 2 | 1 |
| 1 | 0.05 | 4 | 3 |
| 1 | 0.10 | 6 | 5 |
| 1 | 0.50 | 10 | 8 |
| 1 | 1 | 12 | 11 |
| 1 | 2 | 13 | 12 |
| 1 | 10 | 14 | 14 |
| 1 | 50 | 15 | 14 |
| 1 | 100 | 15 | 15 |
| 0 | 1 | 16 | 16 |

Test 3.

This test was carried out for determining the influence of tableting on the number of viable microbial cells in the tablets containing viable microbial cells.

1) Preparation of the Samples

Microbial powder (2 parts) of *Blifdobactenum longum* M-8201 (FERM P-6548) (number of viable microbial cells: $100 \times 10^6$ cells/g; manufactured by Morinaga Milk Industry) and 3 parts of glycerol fatty acid ester (manufactured by Riken Vitamin) as a lubricant were added to 95 parts of a mixture where lactulose powder (manufactured by Morinaga Milk Industry) and lactoferrin powder (manufactured by Morinaga Milk Industry) were compounded in a ratio of 0.5:1, followed by homogeneously mixing to prepare a tablet material (the number of viable microbial cells $2 \times 10^8$ cells/g) (Sample 4).

In addition microbial powder (2 parts) of *Bifidobacterum longum* (the number of viable microbial cells: $100 \times 10^8$ cell/g, manufactured by Morinaga Milk Industry) and 3 parts of glycerol fatty acid ester (manufactured by Riken Vitamin) as a lubricant were added to 95 parts of a mixture where maltitol powder (manufactured by Towa Kasei Kogyo) and lactoferrin powder (manufactured by Morinaga Milk Industry) were compounded in a ratio of 0.5:1 followed by homogeneously mixing to prepare a tableting material (the number of viable microbial cells: $2 \times 10^8$ cells/g) (Sample 5).

Each of the above samples was made into tablets with a tableting pressure of 2 tons using a tableting machine of a rotary type (manufactured by Hata Tekkosho) equipped with round pestles for tablets having a diameter of 10 mm whereupon 500 round-shaped tablets each having a diameter of 10 mm and a weight of 0.5 g were prepared for each of the samples.

2) Procedures

An average hardness was measured by the same method as in Test 1. In addition, ten tablets were randomly sampled from the tablets of each of the Samples. The number of viable microbial cells of the bifidobacteria in each tablet were measured by a pour culture. An average number for each Sample was calculated and the numbers of viable microbial cells were compared between Samples of 4 and 5.

3) Results

The results of the test are shown in Table 2 It is apparent from Table 2 that, when lactulose was added (Sample 4), rigid tablets (about 10 kg in average in the horizontal direction and about 8 kg in average in the vertical direction) with nearly no loss of viable microbial cell numbers were obtained. Conversely, in the case of the tablets where maltitol was added (Sample 5), although the number of viable microbial cells rarely decreased as same as in the case of addition of lactulose, hardness in the horizontal direction was about 3 kg in average and in the vertical direction was about 1 kg in average making the tablets very fragile.

Accordingly, it has been found that, when a material consisting of viable microbial powder of lactic acid bacteria, lactoterrin and lactulose is made into tablets, rigid tablets are able to be produced with nearly no decrease in the number of viable microbial cells.

Incidentally, the same tests were carried out for the tablets prepared by changing the types of lactoferrin, lactulose, viable microbial powder and tableting machine whereupon nearly the same result was obtained.

TABLE 2

| Items Tested | Sample 4 | Sample 5 |
|---|---|---|
| Numbers of Viable Cells before Tableting ($\times 10^8$/g) | 2.0 | 2.0 |
| Numbers of Viable Cells after Tableting ($\times 10^8$/g) | 1.8 | 1.7 |
| Hardness of Tablet (kg) (in Honzontal Direction) | 9.7 | 2.8 |
| ditto (in Vertical Direction) | 8.2 | 1.1 |

The present invention will now be further concretely illustrated by way of the following Examples although this invention is not limited to the following Examples only. Incidentally, the lactic acid bactena (what is called lactobacillus) used in the Examples were prepared according to the following Referential Examples 1–4.

Referential Example 1.

*Bifidobactenum longum* M-8201 (FERM P-6548) was subjected to a subculture for ten generations using an ABCM medium (manufactured by Eiken Kagaku) to which glucose was added, then inoculated to 50 liters of a synthetic medium consisting of glucose, yeast extract, peptone and phosphate and incubated at 37° C. for 14 hours. The cultured medium was centrifuged to collect the cells, 500 ml of a dispersing medium where 100 g of glutamic acid (manufactured by Wako Pure Chemical) and 50 g of sucrose were dissolved in water was added to one liter of the resulting cell solution and the mixture was freeze-dried.

The resulting powdery cells (275 g) were mixed and diluted with 2 kg of lactose (manufactured by Wako Pure Chemical) and 2.5 kg of dried corn starch (manufactured by Matsutani Kagaku Kogyo) to give about 4.7 kg of powdery cells (what is called microbial powder) of *Bifidobactedum longum* (the number of viable cells: $110 \times 10^8$ cells/g).

Referential Example 2.

The same method as in Referential Example 1 was carried out except that *Streptococcus faecalis* ATCC-19433 was used to give about 4.0 kg of powdery cells of *Streptococcus faecalls* (the number of viable cells; $230 \times 10^8$ cells/g).

Referential Example 3.

The same method as in Referential Example 1 was carded out except that *Lactobacillus acidophilus* ATCC-4356 was used to give about 4.5 kg of powdery cells of *Lactobacillus acidophilus* (numbers of viable cells: $340 \times 10^8$ cells/g).

Referential Example 4.

The same method as in Referential Example 1 was carried out except that *Leuconostoc cremois* ATCC-1 9254 was used to give about 3.5 kg of powdery cells of *Leuconostoc cremoris* (the number of viable cells: $50 \times 10^8$ cells/g).

EXAMPLE 1

Lactoferrin (40 kg) (manufactured by Morinaga Milk Industry), 40 kg of lactulose (manufactured by Morinaga Milk Industry), 8.5 kg of erythritol (manufactured by Nikken Kagaku), 8 kg of maltitol (manufactured by Towa Kasei Kogyo), 0.1 kg of stevia (manufactured by Nippon Seishi), 3 kg of glycerol fatty acid ester (manufactured by Riken Vitamin) and 0.4 kg of yogurt flavor (manufactured by Hasegawa Koryo) were homogeneously mixed and made into tablets with a tableting pressure of 2 tons using a tableting machine of a rotating table type (manufactured by Hata Tekkosho) to give 195,000 triangle-shaped tablets each weighing 0.5 g.

The hardness of the resulting tablets was measured by the same method as in Test 1 and found to be 10 kg in average in the horizontal direction and 9 kg in average in the vertical direction.

EXAMPLE 2

The same method as in Example 1 was carried out except that 76.2 kg of lactoferrin (manufactured by Morinaga Milk Industry) and 3.8 kg of lactulose (manufactured by Morinaga Milk Industry) were used to give 195,000 triangle-shaped tablets each weighing 0.5 g.

The hardness of the resulting tablets was measured by the same method as in Test 1 and found to be 6 kg in average in the horizontal direction and 4 kg in average in the vertical direction.

EXAMPLE 3

The same method as in Example 1 was carried out except that 72.7 kg of lactoferrin (manufactured by Morinaga Milk Industry) and 7.3 kg of lactulose (manufactured by Morinaga Milk Industry) were used to give 195,000 triangle-shaped tablets each weighing 0.5 g.

The hardness of the resulting tablets was measured by the same method as in Test 1 and found to be 7 kg in average in the horizontal direction and 7 kg in average in the vertical direction.

EXAMPLE 4

The same method as in Example 1 was carried out except that 0.8 kg of lactoferrin (manufactured by Morinaga Milk Industry) and 80 kg of lactulose (manufactured by Morinaga Milk Industry) were used to give 195,000 triangle-shaped tablets each weighing 0.5 g.

The hardness of the resulting tablets was measured by the same method as in Test 1 and found to be 14 kg in average in the horizontal direction and 13 kg in average in the vertical direction.

EXAMPLE 5

Lactoferrin (30 kg) (manufactured by Morinaga Milk Industry), 30 kg of lactulose (manufactured by Morinaga Milk Industry), 8.5 kg of erythritol (manufactured by Nikken Kagaku), 8 kg of maltitol (manufactured by Towa Kasei Kogyo), 0.1 kg of stevia (manufactured by Nippon Seishi), 20 kg of powdery cells of *Bifidobacterium longum* manufactured by the same method as in Referential Example 1, 3 kg of glycerol fatty acid ester (manufactured by Riken Vitamin) and 0.4 kg of yogurt flavor (manufactured by Hasegawa Koryo) were homogeneously mixed and made into tablets with a tableting pressure of 2 tons using a tableting machine of a rotating table type (manufactured by Hata Tekkosho) to give 195,000 triangle-shaped tablets each weighing 0.5 g.

The hardness of the resulting tablets was measured by the same method as in Test 1 and found to be 10 kg in average in the horizontal direction and 9 kg in average in the vertical direction. The number of viable microbial cells were $22 \times 10^8$ cellsig before tableting and $21 \times 10^8$ cells/g after tableting

EXAMPLE 6

The same method as in Example 5 was carried out except that 5.71 kg of lactoferrin (manufactured by Morinaga Milk Industry) and 0.29 kg of lactulose (manufactured by Morinaga Milk Industry) were used and the amounts of the other ingredients were made one-tenth to give 18,000 triangle-shaped tablets each weighing 0.5g.

The hardness of the resulting tablets was measured by the same method as in Test 1 and found to be 4 kg in average in the horizontal direction and 3 kg in average in the vertical direction. The number of viable microbial cells were $22 \times 10^8$ cells/g before tableting and $20 \times 10^8$ cells/g after tableting.

EXAMPLE 7

The same method as in Example 5 was carded out except that 5.46 kg of lactoferrin (manufactured by Morinaga Milk Industry) and 0.546 kg of lactulose (manufactured by Morinaga Milk Industry) were used and the amounts of the other ingredients were made one-tenth to give 18,000 triangle-shaped tablets each weighing 0.5g.

The hardness of the resulting tablets was measured by the same method as in Test 1 and found to be 5 kg in average in the horizontal direction and 5 kg in average in the vertical direction. The number of viable microbial cells were $22 \times 10^8$ cells/g before tableting and $21 \times 10^8$ cells/g after tableting.

EXAMPLE 8

The same method as in Example 5 was carried out except that 0.2 kg of lactoferrin (manufactured by Morinaga Milk Industry) and 20 kg of lactulose (manufactured by Morinaga Milk Industry) were used and the amounts of the other ingredients were made one-third to give 64,000 triangle-shaped tablets each weighing 0.5 g.

The hardness of the resulting tablets was measured by the same method as in Test 1 and found to be 15 kg in average in the horizontal direction and 15 kg in average in the vertical direction. The Number of viable microbial cells were $22 \times 10^8$ cells/g before tableting and $20 \times 10^8$ cells/g after tableting.

EXAMPLE 9

The same method as in Example 5 was carried out except that 2 kg of powdery cells of *Streptococcus feecalis* manufactured by the same method as in Referential Example 2 were used and the amounts of the other ingredients were made one-tenth to give 18,000 triangle-shaped tablets each weighing 0.5 g.

The hardness of the resulting tablets was measured by the same method as in Test 1 and found to be 10 kg in average in the horizontal direction and 10 kg in average in the vertical direction. The number of viable microbial cells were $46 \times 10^8$ cells/g before tableting and $44 \times 10^8$ cells/g after tableting.

EXAMPLE 10

The same method as in Example 5 was carried out except that 10 kg of powdery cells of *Lactobacillus acidophilus* manufactured by the same method as in Referential Example 3 were used and the amounts of the other ingredients were made one half to give 98,000 triangle-shaped tablets each weighing 0.5 g.

The hardness of the resulting tablets was measured by the same method as in Test 1 and found to be 10 kg in average in the horizontal direction and 9 kg in average in the vertical direction. The number of viable microbial cells were 68×10$^8$ cells/g before tableting and 62×10$^8$ cells/g after tableting.

EXAMPLE 11

The same method as in Example 5 was carried out except that 10 kg of powdery cells of *Leuconostoc cremorins* manufactured by the same method as in Referential Example 4 were used and the amounts of the other ingredients were made one half to give 98,000 triangle-shaped tablets each weighing 0.5 g.

The hardness of the resulting tablets was measured by the same method as in Test 1 and found to be 11 kg in average in the horizontal direction and 9 kg in average in the vertical direction. The number of viable microbial cells were 10×10$^8$ cells/g before tableting and 9×10e cells/g after tableting.

EXAMPLE 12

The same method as in Example 5 was carried out except that 3 kg of lactoferrin (manufactured by Morinaga Milk Industry) and 3 kg of lactulose (manufactured by Morinaga Milk Industry) were previously mixed, followed by granulating using a fluidized granulating drier (manufactured by Okawara Seisakusho) and the amounts of the other ingredients were made one tenth to give 18,000 triangle-shaped tablets each weighing 0.5 g.

The hardness of the resulting tablets was measured by the same method as in Test 1 and found to be 12 kg in average in the horizontal direction and 11 kg in average in the vertical direction. The number of viable microbial cells were 22×10$^8$ cells/g before tableting and 20×10$^8$ cells/g after tableting.

EXAMPLE 13

The same method as in Example 5 was carried out except that 6 kg of lactoferrin (manufactured by Morinaga Milk Industry), 6 kg of lactulose (manufactured by Morinaga Milk Industry), 1.7 kg of erythritol (manufactured by Nikken Kagaku), 1.6 kg of maltitol (manufactured by Towa Kasei Kogyo) and 0.02 kg of stevia (manufactured by Nippon Seishi) were previously mixed, followed by granulating using a fluidized granulating drier (manufactured by Okawara Seisakusho) and the amounts of the other ingredients were made one-fifth to give 38,000 triangle-shaped tablets each weighing 0.5 g.

The hardness of the resulting tablets was measured by the same method as in Test 1 and found to be 12 kg in average in the horizontal direction and 11 kg in average in the vertical direction. The number of viable microbial cells were 22×10$^8$ cells/g before tableting and 20×10$^8$ cells/g after tableting.

EXAMPLE 14

Lactoferrin (8 kg) (manufactured by Morinaga Milk Industry), 4 kg of laclulose (manufactured by Morinaga Milk Industry), 1.7 kg of erythritol (manufactured by Nikken Kagaku), 1.6 kg of maltitol (manufactured by Towa Kasei Kogyo), 0.02 kg of stevia (manufactured by Nippon Seishi), 1 kg of powdery cells of *Bifidobactenum longum* manufactured by the same method as in Referential Example 1, 1 kg of powdery cells of *Streplococcus faecalis* manufactured by the same method as in Referential Example 2,1 kg of powdery cells of *Lactobacillus acidophilus* manufactured by the same method as in Referential Example 3, 1 kg of powdery cells of *Leuconostoc cremoris* manufactured by the same method as in Referential Example 4, 0.6 kg of glycerol fatty acid ester (manufactured by Riken Vitamin) and 0.08 kg of yogurt flavor (manufactured by Hasegawa Koryo) were homogeneously mixed and made into tablets with a tableting pressure of 2 tons using a tableting machine of a rotating table type (manufactured by Hata Tekkosho) to give 38,000 football-shaped tablets each weighing 0.5 g.

The hardness of the resulting tablets was measured by the same method as in Test 1 and found to be 9 kg in average in the horizontal direction and 8 kg in average in the vertical direction. The number of viable microbial cells were 37×10$^8$ cells/g before tableting and 34×10$^8$ cells/g after tableting.

EXAMPLE 15

Lactoferrin (5.45 kg) (manufactured by Morinaga Milk Industry), 54.5 kg of lactulose (manufactured by Morinaga Milk Industry), 8.5 kg of erythritol (manufactured by Nikken Kagaku), 8 kg of maltitol (manufactured by Towa Kasei Kogyo) and 0.1 kg of stevia (manufactured by Nippon Seishi) were previously mixed and granulated using a fluidized granulating drier (manufactured by Okawara Seisakusho), then 5 kg of powdery cells of *Bifidobacterium longum* manufactured by the same method as in Referential Example 1, 5 kg of powdery cells of *Streptococcus faecalis* manufactured by the same method as in Referential Example 2, 5 kg of powdery cells of Lactobacillus acidophilus manufactured by the same method as in Referential Example 3, 5 kg powdery cells of *Leuconostoc cremoris* manufactured by the same method as in Referential Example 4, 3 kg of glycerol fatty acid ester (manufactured by Riken Vitamin) and 0.4 kg of yogurt flavor (manufactured by Hasegawa Koryo) were added thereto, homogeneously mixed therewith and made into tablets with a tableting pressure of 2 tons using a tableting machine of a rotating table type (manufactured by Hata Tekkosho) to give 195.000 heart-shaped tablets each weighing 0.5 g.

The hardness of the resulting tablets was measured by the same method as in Test 1 and found to be 13 kg in average in the horizontal direction and 12 kg in average in the vertical direction. The number of viable microbial cells were 37×10$^8$ cells/g before tableting and 33×10$^8$ cells/g after tableting.

In accordance with this invention, lactoferrin having excellent pharmacological actions such as protection of infection and immunopotentiation can be produced as rigid tablets.

The lactoferrin tablet of this invention can be produced by using the conventional apparatuses and, in addition, have high hardness and, accordingly, they do not adhere to the inner wall of the oral cavity upon taking and have a favorable taste as well. Further, no excessive tableting pressure is needed in their production and, therefore, many viable cells of lactic acid bacteria can be contained therein in spite of the fact that the product is a rigid lactoferrin-containing tablet.

What is claimed is:

1. A lactoferrin tablet comprising, as active ingredients, lactoferrin and lactulose, and having a horizontal hardness of at least 4 kg and a vertical hardness of at least 3 kg.

2. The lactoferrin tablet according to claim 1, wherein the horizontal hardness is 6–14 kg and the vertical hardness is 5–14 kg.

3. The lactoferrin tablet according to claim 2, which comprises at least 0.05 part by weight of lactulose per 1 part by weight of lactoferrin.

4. The lactoferrin tablet according to claim 1, which comprises at least 0.05 part by weight of lactulose per 1 part by weight of lactoferrin.

5. A lactoferrin tablet comprising, as active ingredients, lactoferrin and lactulose, and at least one kind of microbial powder selected from the group consisting of microorganisms belonging to Bifidobacterieum, microorganisms belonging to Lactobacillus, microorganisms belonging to Streptococcus, microorganisms belonging to Pediococcus, and microorganisms belonging to Leucostoc, said lactoferrin tablet having a horizontal hardness of at least 4 kg and a vertical hardness of at least 3 kg.

6. The lactoferrin tablet according to claim 5, wherein the horizontal hardness is 6–14 kg and the vertical hardness is 5–14 kg.

7. The lactoferrin tablet according to claim 6, which comprises at least 0.05 part by weight of lactulose per 1 part by weight of lactoferrin.

8. The lactoferrin tablet according to claim 5, which comprises at least 0.05 part by weight of lactulose per 1 part by weight of lactoferrin.

* * * * *